United States Patent [19]

Wang et al.

[11] Patent Number: 5,795,470
[45] Date of Patent: Aug. 18, 1998

[54] MAGNETIC SEPARATION APPARATUS

[75] Inventors: Yuzhou Wang, Wayne; Weixin Tang, Lansdale; Paul A. Liberti, Huntingdon Valley, all of Pa.

[73] Assignee: Immunivest Corporation, Wilmington, Del.

[21] Appl. No.: 482,636

[22] Filed: Jun. 7, 1995

Related U.S. Application Data

[63] Continuation-in-part of Ser. No. 228,818, Apr. 18, 1994, Pat. No. 5,541,072, and Ser. No. 6,071, Jan. 15, 1993, Pat. No. 5,466,574, which is a continuation-in-part of Ser. No. 674,678, Mar. 25, 1991, Pat. No. 5,186,827.

[51] Int. Cl.$^6$ ............................................. B01D 35/06
[52] U.S. Cl. ................................. 210/222; 210/456
[58] Field of Search ........................... 210/222, 223, 210/456; 209/224, 232; 335/302, 304, 306; 96/1, 2

[56] References Cited

U.S. PATENT DOCUMENTS

| | | |
|---|---|---|
| 564,858 | 7/1896 | Whitacre et al. . |
| 3,326,374 | 6/1967 | Jones . |
| 3,402,820 | 9/1968 | Lohmann . |
| 3,567,026 | 3/1971 | Kolm . |
| 3,608,718 | 9/1971 | Aubrey et al. . |

(List continued on next page.)

FOREIGN PATENT DOCUMENTS

| | | |
|---|---|---|
| 2294888 | 4/1989 | Australia . |
| 0030087 | 6/1981 | European Pat. Off. . |
| 0149565 | 7/1985 | European Pat. Off. . |
| 0230768 | 8/1987 | European Pat. Off. . |
| WO9007380 | 4/1990 | WIPO . |
| WO9109938 | 4/1991 | WIPO . |
| WO9116452 | 10/1991 | WIPO . |

OTHER PUBLICATIONS

Forrest et al., "Magnetic Particle Radioimmunoassay" in Immunoassays for Clinical Chemistry, pp. 147–162, Hunter et al. eds Churchill Livingston (1983).

The Properties of Magnetic Supports in Relation to Immobilized Enzyme Reactors, Robinson et al., Biotechnology and Bioengineering, vol. XV (1973).

The Dynal MPC-1 (manufactured by DYNAL, Inc., Great Neck, NY) product information sheet (1987).

BioMag Separator (manufactured by Advanced Magnetics, Inc., Cambridge MA) catalog pages (3 sheets).

Magnetic Separator (manufactured by Ciba–Corning Medical Diagnostics, Wampole, MA) catalog cover and catalog pages (2 sheets).

Magnetic Separator (Made by Milteny Biotech. GmbH, Gladbach, Germany) Product information sheet.

(List continued on next page.)

*Primary Examiner*—Matthew O. Savage
*Attorney, Agent, or Firm*—Dann, Dorfman, Herrell & Skillman, P.C.

[57] ABSTRACT

A magnetic separation apparatus is disclosed herein. The apparatus includes a flow-through vessel defining a plenum and an inlet port for introducing fluid into the plenum. A hydrodynamic damping structure is provided between the inlet port and plenum for reducing turbulence in the fluid. A mounting device is provided with a slot therein for supporting and receiving the vessel. The mounting device also supports a first array of magnets along one side of the slot and arranged adjacent one another to face the slot with alternating polarity, and a second array of magnets along the opposite side of the slot from the first array arranged adjacent one another to face the slot with alternating polarity and confronting and magnetically opposing the magnets in the first array. The first and second arrays of magnets produce a magnetic field within the plenum having a field strength that is maximum at a location at the interior surface of a wall of the vessel and that is minimum at a geometrical center of the plenum so that magnetic particles in the fluid are attracted to and immobilized on the inner surface of the vessel.

1 Claim, 10 Drawing Sheets

U.S. PATENT DOCUMENTS

| | | |
|---|---|---|
| 3,676,337 | 7/1972 | Kolm . |
| 3,902,994 | 9/1975 | Maxwell et al. . |
| 3,970,518 | 7/1976 | Giaever . |
| 3,987,649 | 10/1976 | Eddelman . |
| 4,018,886 | 4/1977 | Giaever . |
| 4,141,687 | 2/1979 | Forrest et al. . |
| 4,209,394 | 6/1980 | Kelland . |
| 4,230,685 | 10/1980 | Senyei et al. . |
| 4,265,746 | 5/1981 | Zimmerman, Sr. et al. ............ 210/222 |
| 4,265,755 | 5/1981 | Zimmerman ............................ 210/222 |
| 4,267,234 | 5/1981 | Rembaum . |
| 4,452,773 | 6/1984 | Molday . |
| 4,498,987 | 2/1985 | Inaba . |
| 4,510,244 | 4/1985 | Parks et al. . |
| 4,554,088 | 11/1985 | Whitehead et al. . |
| 4,659,678 | 4/1987 | Forrest et al. . |
| 4,663,029 | 5/1987 | Kelland et al. . |
| 4,672,040 | 6/1987 | Josephson . |
| 4,714,680 | 12/1987 | Civin . |
| 4,795,698 | 1/1989 | Owen et al. . |
| 4,895,650 | 1/1990 | Wang . |
| 4,904,391 | 2/1990 | Freeman . |
| 4,910,148 | 3/1990 | Sorensen . |
| 4,935,147 | 6/1990 | Ullman et al. . |
| 4,946,590 | 8/1990 | Hertzog . |
| 4,988,618 | 1/1991 | Li et al. . |
| 5,055,190 | 10/1991 | Hayes et al. . |
| 5,061,620 | 10/1991 | Tsukamoto et al. . |
| 5,070,852 | 12/1991 | Po et al. ................................. 123/538 |
| 5,108,933 | 4/1992 | Liberti et al. . |
| 5,129,382 | 7/1992 | Stamps, Sr. et al. ................... 123/538 |
| 5,186,827 | 2/1993 | Liberti et al. . |
| 5,200,084 | 4/1993 | Liberti et al. . |
| 5,466,574 | 11/1995 | Liberti et al. . |
| 5,584,994 | 12/1996 | Hattori et al. .......................... 210/222 |

OTHER PUBLICATIONS

High Gradient Magnetic Separation Therory and Applications, R.R. Oder, IEEE Transactions on Magnetics, vol. MAG–12, No. 5, pp. 428–435, Sep., 1976.

Magnetite–Protein Conjugates for the Separation of Cells by High Gradient Magnetic Filtration, C.S. Owen et al., Cell Separation Methods and Selected Applications, vol. 4, 1987.

Magnetic Separation Techniques: Their Application to Medicine, J.T. Kemshead et al., Molecular and Cellular Biochemistry 67: 11–18 (1985).

Magnetic Solid–Phase Radioimmunoassay, L.S. Hersh et al., Clinica Chimica Acta 63:69–72 (1975).

Ivan Damjanov, "Biology of Disease: Lectin Cytochemistry and Histochemistry", Lab. Invest. 57:5–20 (1987).

Magnetic Separator System (manufactured by Serono Diagnostics, Norwell, MA) catalog pages (2 sheets).

Hancock, J.P. et al., "A rapid and highly selective approach to cell separations using an immunomagnetic colloid", J. of Immunol. Meth. 164:51–60 (1993).

Liberti P.A. et al., "Ferrofluid as a matrix for magnetic separations", 1st John Ugelstad Conf., pp. 47–61, (1991).

Areman, E.M., et al., Bone Marrow and Stem Cell Processing: A Manual of Current Techniques, pp. 267–285, (1992).

Bieva, C.J. et al., "Malignant Leukemic cell separation by iron colloid immunomagnetic adsorption", Exp. Hematol. 17:914–920, (1988).

Powers, F.J., et al., Separation of small–cell lung cancer cells from bone marrow using immunomagnetic beads, in Bone Marrow Processing and Purging, A.P. Gee ed., pp. 257–267.

Rhodes, E.G.H. et al., "Peanut Agglutinin purging and magnetic microspheres" in Advances in Bone Marrow Purging, pp. 139–146, (1992).

Okarma, T. et al., The AIS collector: a new technology for stem cell purification, Advances in Bone Marrow Purging and Processing, pp. 487–504, (1992).

Reading, C.L. et al., "Magnetic affinity colloid elimination of specific cell populations from bone marrow", in Bone Marrow Transplantation: Proceedings of the 3rd International Symposium: Autologous Bone Marrow Transplantation, Dec. 4–5, 1986, pp. 133–142.

Molday, R.S. et al., "Immunospecific ferromagnetic iron––dextran reagents for the labeling and magnetic separation of cell." J. Immunol. Meth. 52:353–367 (1982).

Straus, L.C. et al., "Selection of normal hematopoietic stem cells for bone marrow transplantation using immunomagnetic microspheres and CD34 antibody." Am. J. Ped. Hematology/Oncology 13:217–221.

Trickett, A.E., et al., "Comparison of magnetic particles for immunomagnetic bone marrow purging using an acute lymphoblastic leukemia model", Transplantation Procedings 22:2177–2178.

Padanabhan, R., et al., "Purification of transiently transfected cells by magnetic–affinity cell sorting", J. of Immunomagnetics 16:91–102 (1989).

Brun, A., et al., "A new method for isolation of reticulocytes: positive selection of human reticulocytes by immunomagnetic separation" Blood 76:2397–2403 (1990).

Ganshirt–Ahlert, D., et al., "Detection of Fetal Trisomies 21 and 18 from maternal blood using triple gradient and magnetic cell sorting". Am. J. Immunol. 30:194–201 (1993).

Muir, P., et al., "Rapid diagnosis of enterovirus infection by magnetic bead extraction and polymerase chain reaction detection of enterovirus RNA in clinical specimens". J. Clin. Micro. Jan. 1993 pp. 31–38.

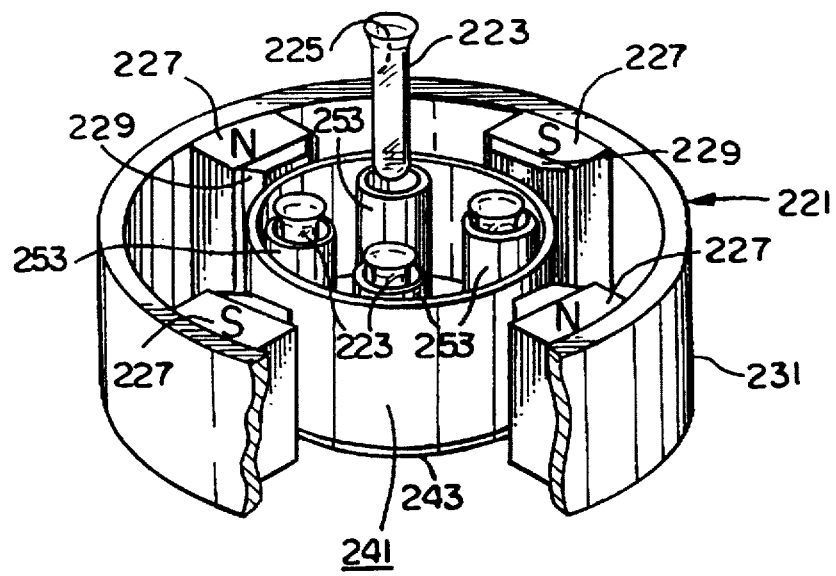
FIG. 4
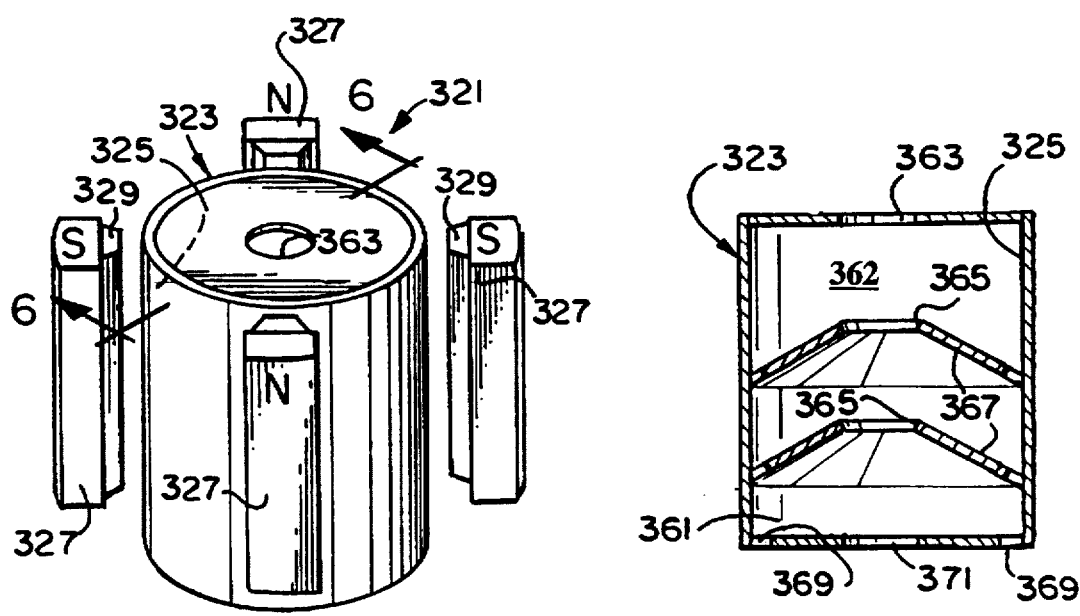
FIG. 5
FIG. 6

MAGNETIC SEPARATION APPARATUS

CROSS-REFERENCE TO RELATED APPLICATIONS

This is a continuation in part of U.S. application Ser. No. 08/006,071, filed Jan. 15, 1993, now U.S. Pat. No. 5,466,574, which is a continuation in part of U.S. application Ser. No. 07/674,678, filed Mar. 25, 1991, now U.S. Pat. No. 5,186,827.

This is also a continuation in part of U.S. application Ser. No. 08/228,818, filed Apr. 18, 1994, now U.S. Pat. No. 5,541,072.

The full disclosures of each of the aforementioned patent and applications are incorporated by reference herein.

FIELD OF THE INVENTION

The present invention relates to improvements in magnetic separators and methods of separation of magnetic particles and/or magnetic-associated entities from non-magnetic associated entities and media, having particular utility in various diagnostic, therapeutic and industrial procedures involving specific reactions.

BACKGROUND OF THE INVENTION

Various laboratory and clinical procedures employ biospecific affinity reactions. Such reactions are commonly employed in diagnostic testing of biological samples, or for the separation of a wide range of target substances, especially biological entities such as cells, proteins, nucleic acid sequences, and the like.

Various methods are available for analyzing or separating the above-mentioned target substances based upon complex formation between the substance of interest and another substance to which the target substance specifically binds. Separation of complexes from unbound material may be accomplished gravitationally, e.g. by settling, or, alternatively, by centrifugation of finely divided particles or beads coupled to the target substance. If desired, such particles or beads may be made magnetic to facilitate the bound/free separation step. Magnetic particles are well known in the art, as is their use in immune and other bio-specific affinity reactions. See, for example, U.S. Pat. No. 4,554,088 and *Immunoassays for Clinical Chemistry*, pp. 147–162, Hunter et al. eds., Churchill Livingston, Edinborough (1983). Generally, any material which facilitates magnetic or gravitational separation may be employed for this purpose.

Small magnetic particles have proved to be quite useful in analyses involving biospecific affinity reactions, as they are conveniently coated with biofunctional polymers, e.g., proteins, provide very high surface areas and give reasonable reaction kinetics. Magnetic particles ranging from 0.7–1.5 microns have been described in the patent literature, including, by way of example, U.S. Pat. Nos. 3,970,518; 4,018,886; 4,230,685; 4,267,234; 4,452,773; 4,554,088; and 4,659,678. Certain of these particles are disclosed to be useful solid supports for immunologic reagents.

Small magnetic particles, such as those mentioned above, generally fall into two broad categories. The first category includes particles that are permanently magnetizable, or ferromagnetic; and the second comprises particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction.

In contrast to larger particles, the tendency of colloidal superparamagnetic particles to remain in suspension, in conjunction with their relatively weak magnetic responsiveness, requires the use of high-gradient magnetic separation (HGMS) techniques in order to separate such particles from a fluid medium in which they are suspended. In HGMS systems, the gradient of the magnetic field, i.e. the spatial derivative, exerts a greater influence upon the behavior of the suspended particles than is exerted by the strength of the field at a given point.

U.S. Pat. No. 4,795,698 to Owen et al. relates to polymer-coated, sub-micron size colloidal superparamagnetic particles. The '698 patent describes the manufacture of such particles by precipitation of a magnetic species in the presence of a biofunctional polymer. The structure of the resulting particles, referred to herein as single-shot particles, has been found to be a micro-agglomerate in which one or more ferromagnetic crystallites having a diameter of 5–10 nm are embedded within a polymer body having a diameter on the order of 30–100 nm. These particles exhibit true colloidal behavior and do not exhibit an appreciable tendency to separate from aqueous suspensions for observation periods as long as several days to several months.

Another method for producing superparamagnetic colloidal particles is described in U.S. application Ser. No. 07/397,106. In contrast to the particles described in the '698 patent, these latter particles are produced by directly coating a biofunctional polymer onto a pre-formed superparamagnetic crystallite. The resulting particles, referred to herein as DC particles, exhibit a significantly larger magnetic moment than single-shot particles of the same overall size.

Magnetic separation techniques are known wherein a magnetic field is applied to a fluid medium in order to separate ferromagnetic bodies from the fluid medium. For example, micron size ferromagnetic, i.e., permanently magnetized, particles are readily removed from solution by means of commercially available magnetic separation devices. These devices employ a single relatively inexpensive permanent magnet located external to a container holding the test medium. Examples of such magnetic separators are the MAIA Magnetic Separator manufactured by Serono Diagnostics, Norwell, Mass., the DYNAL MPC-1 manufactured by DYNAL, Inc., Great Neck, N.Y. and the BioMag Separator, manufactured by Advanced Magnetics, Inc., Cambridge, Mass. A specific application of a device of this type in performing magnetic solid-phase radioimmunoassay is described in L. Hersh et al., *Clinica Chemica Acta*, 63: 69–72 (1975). A similar magnetic separator, manufactured by Ciba-Corning Medical Diagnostics, Wampole, Mass. is provided with rows of bar magnets arranged in parallel and located at the base of the separator. This device accommodates 60 test tubes, with the closed end of each tube fitting into a recess between two of the bar magnets.

An automated continuous-flow radioimmunoassay system employing cellulose-coated magnetic particles is described in U.S. Pat. No. 4,141,687. The automated system exemplified in the '687 patent includes elaborate electromagnetic traps which are operable in a pre-determined sequence by a programmer device under the control of a sample detector.

The above-described magnetic separators have the disadvantage that the magnetic particles attracted toward the magnets tend to form in multiple layers on the inner surface of the sample container where they are entrapped along with impurities that are difficult to remove even with vigorous washing.

SUMMARY OF THE INVENTION

According to one aspect of the invention magnetic separation apparatus and methods are provided, which are capable of generating a high gradient magnetic field within a non-magnetic test medium to separate magnetically responsive colloidal particles from the test medium. Unlike relatively larger size magnetic particles which tend to settle out of an aqueous medium, magnetically responsive colloidal particles remain suspended in an aqueous medium for an indefinite period, thereby making them readily accessible to target substances.

One magnetic separator of the invention comprises a magnetic means capable of generating a high gradient magnetic field in a gap or receptacle into which at least one vessel containing a test medium may be placed. The container preferably has a peripheral wall with an internal surface area and is adapted to receive the test medium with the magnetically responsive colloidal particles therein (hereinafter "the test medium being separated"). As will be described in further detail below, the magnetic field gradient generating means is disposed outside the container and provides an "open" field gradient inside the container, wherein the magnetic field is stronger in the test medium along the internal wall surface of the container than it is in the test medium most distant from the wall.

If the test medium being separated is in a steady state, e.g., in a batch-type operation, suitable containers include microtiter wells, test tubes, capillary tubes closed at one end, or other non-magnetic cylindrical walled vessels defining a chamber for performing the desired separation. Furthermore, a plurality of test samples may be processed simultaneously through the use of a carrier capable of holding more than one sample container. In a preferred form, the carrier includes means for holding a plurality of containers around the periphery of the carrier.

If the test medium is to pass continuously through the separator, a suitable container is a conduit or tube having openings at each end. Such containers are preferably non-magnetic, e.g., glass or plastic, and of cylindrical configuration. Preferably, the container has an inlet opening at one end for receiving the test medium which is exposed to the high magnetic field gradient at the center portion of the container. In this particular embodiment, the container may also have one or more non-magnetic baffles spaced apart within the container between the two ends. The baffles are dimensioned to restrict the cross-sectional area of the passageway in which the test medium flows through the container to a region surrounding the axis. The baffles are preferably inclined radially downwardly along the direction of flow, to guide toward the wall any magnetically responsive colloidal particles coming into contact therewith. The conduit preferably has laterally spaced apart outlet means disposed at the end opposite the inlet. One outlet means may be provided along the periphery of the outlet end of the container for collecting the magnetic particles. Another outlet means is centrally positioned at the outlet end for discharging the test medium.

In a particularly preferred embodiment, the magnetic field generating means may comprise multiple permanent magnets or electromagnets. The magnets are arranged so as to define a gap or receptacle which accommodates the container. In this embodiment, the polarity and positioning of the magnets located on the opposite sides of the receptacle are such as to produce flux lines which generate a high gradient magnetic field within the test medium in the container. The magnets may be housed in a ferromagnetic yoke which serves to enhance the field strength produced by the apparatus. The magnetic field gradient produced by this "multipole" arrangement is characterized by a very strong magnetic field near the edge of the receptacle and by virtually no magnetic field at the center of the receptacle. Accordingly, magnetic particles in the test medium adjacent the wall of the container near the edge of the receptacle are subject to considerably greater magnetic force than particles in the test medium furthest from the wall of the container, toward the center of the gap or receptacle where the field strength falls away to zero.

The magnetic means may advantageously comprise magnetic flux concentrating means, particularly, if the gap or receptacle defined by the magnets is much larger than the cross-section of the container or carrier. Suitable for this purpose are pole pieces of various geometries, which are magnetized or magnetizable via an induced field. The magnets comprising the magnetic means may be attached magnetically to, or otherwise joined to the yoke, e.g. by cementing with epoxy, to hold the magnets in a fixed position relative to one another.

The physical properties of the magnetic particles preferably used in the practice of this invention, particularly the relatively small particle size, permit a level of operating efficiency which, insofar as is known, has not been achievable heretofore. Furthermore, by controlling the quantity of magnetic particles added to the test medium relative to the exposed surface area of the wall of the container in contact with the test medium and controlling the orientation of such exposed surface, so as to be substantially coextensive with the contour of the magnetic field, it is possible to cause the magnetic particles to adhere along the exposed surface of the container wall in a substantially single layer, corresponding in thickness to about the size of the magnetic particles and any substance or material borne thereby. By operating in this way, occlusion of non-specifically bound substances in the immobilized magnetic particles is virtually negligible.

In separating magnetically responsive colloidal particles from a non-magnetic test medium in accordance with one aspect of the invention, the particles are initially dispersed in the non-magnetic test medium, forming a stable suspension therein. The magnetic particles typically comprise a receptor capable of specific binding to a target substance of interest in the test medium. If it is desired to separate target substances from test medium in a steady state, a suitable container holding the test medium and the receptor-magnetic particle conjugates are placed in the magnetic separator for batch-wise processing. The external magnetic means disposed around the container produces a magnetic field gradient in the test medium, which causes the magnetic particles to move toward the wall and to become adhered thereto. In the method of the invention which employs a plurality of containers held in a carrier, the magnetic field gradient causes the magnetically responsive colloidal particles in the test medium to move toward and adhere to the wall of each container closest to the magnetic means. In accordance with this method, the orientation of the wall of each container in the carrier relative to the magnetic means may be controllable to cause the particles to adhere more uniformly around a broad portion of the wall of each container.

According to another aspect of the invention, the test medium being separated may be flowed through the separator. The magnetic means is configured relative to the container to produce an "open" field gradient of sufficient strength to pull the magnetic particles from the test medium moving at a pre-determined rate and to adhere them to the wall. The non-magnetic test medium is discharged from the container at an outlet end. In a related embodiment of this method, in which the container includes one or more baffles, the test medium to be separated is caused to flow into the inlet opening at one end of the conduit. As the test medium moves through the conduit, the magnetic particles in the test medium are attracted by the magnetic means toward the wall of the conduit and thereby comes in contact with the baffles. The baffles are arranged to cause the particles to be carried toward the wall of the separation vessel. The magnetic means may be operable to cause the particles to become adhered to the interior wall of the separation vessel, or to permit particles to move down the wall for collection at one or more outlets provided along the periphery of the wall at the end opposite the inlet. The residual test medium may be caused to flow out of the conduit at an outlet laterally spaced from the particle outlet(s) in the center portion of the conduit at the end opposite the inlet end.

In accordance with another aspect of the present invention, we have discovered that a phase phenomenon (that we believe to be due to mutual interactions between suspended magnetic particles and interactions with the suspension medium) can be exploited to produce and maintain a distinct, structured phase of magnetic particles, or ferrophase, within a multi-phase liquid system. The ferrophase can be used to transport target substances from regions of relatively low magnetic field intensity to regions of relatively high magnetic field intensity within an HGMS apparatus. Such transport of the ferrophase can be accomplished at greater speed than the transport of individual magnetic particles within a single liquid phase as has been hitherto obtained in single phase methods. Additionally, this transport mechanism can be exploited to obtain better control of the collection of the magnetic particles, and other entities associated therewith, upon a collection surface within a separation apparatus.

According to another aspect of the invention, a method is provided for separating one or more target substances from a test fluid, which comprises mixing the test fluid with a quantity of magnetic particles to produce a suspension, which includes a magnetic component and a non-magnetic component, the target substance or substances being associated with the magnetic component. A magnetically inert fluid phase is established in a container having a collection surface therein, and the aforementioned suspension is introduced into the container as a distinct phase from the magnetically inert phase. The distinct phase is stable within the container, so that the magnetic and non-magnetic components of the suspension are confined within the distinct phase. A magnetic field is generated in the container, and possesses a sufficiently high intensity in a region adjacent the collection surface to cause disintegration of the distinct phase into its constituent magnetic and non-magnetic components. The distinct phase is attracted toward the collection surface, and the magnetic component of the distinct phase is collected upon the collection surface when the distinct phase disintegrates in the region adjacent the collection surface. The non-magnetic component of the disintegrated phase is removed from the region adjacent the collection surface.

BRIEF DESCRIPTION OF THE DRAWINGS

The foregoing summary as well as the following detailed description of the preferred embodiments of the present invention will be better understood when read in conjunction with the appended drawings, in which:

FIG. 4 is a fragmentary perspective view of a magnetic separation apparatus in which several containers are held in a carrier;

FIG. 5 is a view in perspective of a magnetic separation apparatus in which a flow-through test container is provided with internal baffles;

FIG. 6 is a vertical section through the apparatus of FIG. 5;

DETAILED DESCRIPTION OF THE PREFERRED EMBODIMENTS

Figure 1:
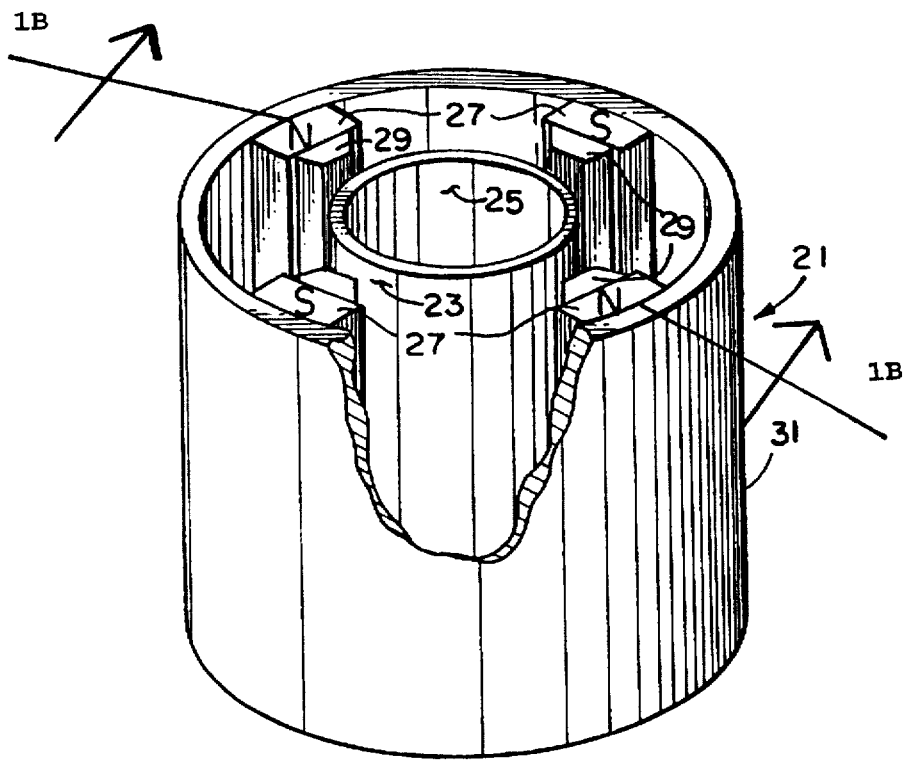
FIG. 1A is a perspective view of a magnetic separation apparatus of the invention, portions of the apparatus being broken away for the purposes of illustration.
FIG. 1B is an elevational sectional diagram of the apparatus of FIG. 1A taken along the line 1B.
FIG. 1C is a plan view of the apparatus shown in FIG. 1A.
Figure 1C:
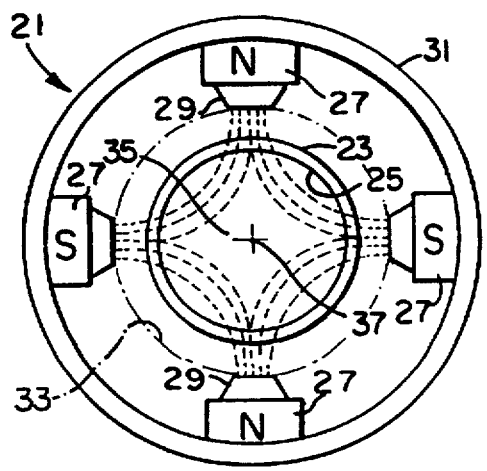
Figure 1B:
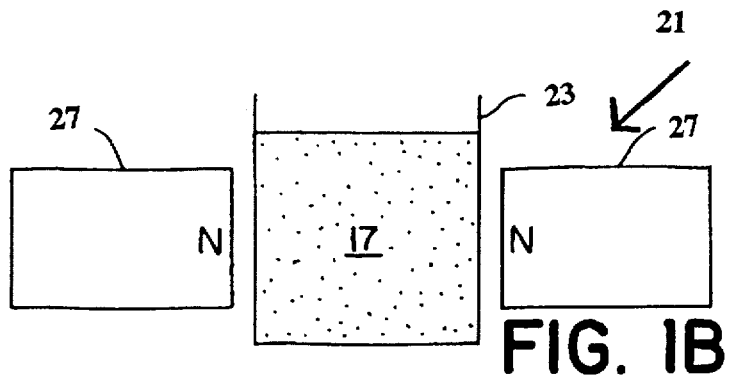

FIGS. 1A–C illustrate an embodiment of a magnetic separator in accordance with the present invention. The separator 21 comprises a container 23 having a peripheral wall 25 and an open top for receiving the test medium. The magnetic separator also includes four magnets 27 which define a gap or receptacle 33 adapted to receive the container. The magnets 27 are equally spaced along the inner surface of cylindrical ferromagnetic housing or yoke 31, on which they are mounted, e.g., by cementing. The magnets may, if desired, be provided with magnetic flux concentrating means, such as pole pieces 29, which permits variation in the lateral dimension of receptacle 33 to accommodate containers of different dimensions, or pole pieces which make the field more uniformly radial.

The arrangement of magnets 27 around the receptacle 33 generates a magnetic field within the receptacle 33 that is substantially uniform along the peripheral wall of the container 23. In other words, the magnetic field within the receptacle 33 is characterized by contours of equal magnetic flux density that are substantially circular within the receptacle 33, and thus the flux density contours are substantially aligned with the periphery of the container 23. Consequently, the angular component of the magnetic field gradient (i.e. along the peripheral wall 25 of the container 23) is substantially zero, and the magnetic flux density gradient is substantially orthogonal to the peripheral wall 25 of the container 23. Additionally, the strength of the magnets and the distance therebetween are selected to produce a high gradient magnetic field sufficient for separating colloidal superparamagnetic particles from a test medium.

The container 23 used to hold the test medium may comprise a microtiter well. The container 23 is positioned substantially coaxially with a gap or receptacle 33 defined by the magnet faces. In that position, the magnetic field strength in the test medium 35 adjacent to the wall approaches the magnetic field strength generated by the magnets. In contrast, there is virtually no magnetic field in the part of the container located along the central axis 37 of receptacle 33, i.e., the test medium most distant from the wall.

The wall of the microtiter well exposed to the test medium provides an ample surface area for adherence of the colloidal magnetic particles. An advantage of the magnetic separator of the invention, when utilized under the conditions described above, is that by appropriately regulating the quantity of magnetic colloid, the particles tend to deposit substantially uniformly upon surfaces in contact with the medium where the magnetic gradient is high. As a result, particles may be caused to be deposited on a broad portion of the internal surface area of the wall in what is effectively a single layer, as opposed to multiple layers or particle agglomerates, which tend to entrap potentially interfering substances, as when formed on a smaller surface, such as occurs in magnetic separators of the prior art.

In experiments using a known separator and employing IgG-bearing magnetic colloid, it was found that when colloid mixed with enzyme was collected on the side of a separation vessel, enzyme became trapped as the colloid began to accumulate in layers. In the practice of this invention, by contrast, the colloidal magnetic particles are sufficiently thinly deposited on the container surface that there is virtually no entrapment of potentially interfering substances. To this end, it is preferable that the portion of the container wall surface in contact with the test medium be selected so that the wall's aggregate collecting surface area is greater, by a factor of about 2, than the surface area that would be occupied by all of the magnetic particles in the test medium, if deposited in a substantially continuous single layer. Thus, in order to promote monolayered collection, the quantity of the magnetic colloid in the separation container must be controlled relative to the size of the target entities and the surface area of the vessel which is available for collection of the biospecifically-bound magnetic particles when the container is placed within the apparatus. Monolayered collection tends to enhance biospecificity of collection relative to multilayered collection in which non-target entities or substances may become entrapped within voids or interstices between layers of collected target entities.

For permanent magnet devices, the magnetic field strength of the external magnetic means (magnets 27 in FIG. 1A) at the pole faces should be in a range of 4–10 KGauss, and more preferably between about 6–8 KGauss. The preferred distance between each magnet and the container shown in FIGS. 1A and 1C is generally about 0.1 cm to about 2.0 cm with the most preferable distance being about 0.5 cm. The field strength of the external magnet or magnets should be great enough, and the distance between the magnets and the container 23 for the test medium short enough to give efficient separation of the magnetic particles. With electro-magnets, considerably higher field strengths at the pole faces, on the order of 15–30 KGauss, can be achieved. In this way, very high gradient fields are obtained.

The receptacle 33 should be formed by the magnets with sufficient excess space for manipulation of the container 23. For example, an elevating mechanism (not shown) may be positioned in the receptacle to raise and support the container 23 in the position illustrated. Alternatively, the housing 31 may have an appropriately shaped bottom support (not shown) for supporting the container within the receptacle.

The pole pieces 29 illustrated in FIG. 1A may be fabricated of any magnetizable material. The pole pieces are shown in the form of magnetized bodies of trapezoidal cross-section, but may be fabricated in other shapes, such as triangular cross-section. These configurations aid in concentrating the magnetic flux emanating from magnets 27. The pole pieces 29 may be held in place on the faces of magnets 27 by magnetic attraction. Alternatively, magnets 27 may be fabricated such that the pole piece is unitary with the body of the magnet.

Figure 3:
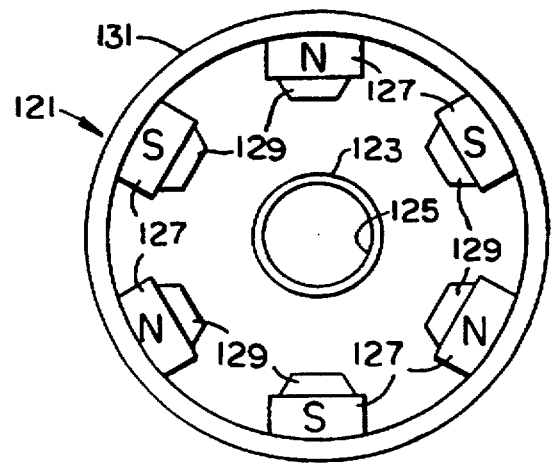
FIG. 3 is a plan view of a magnetic separation apparatus of the invention having a magnetic means comprising six magnets.

FIG. 3 illustrates another embodiment of the magnetic separator of the invention that is similar to the magnetic separator shown in FIGS. 1A–C. The separator 121 shown in FIG. 3 comprises a container 123 in the form of a cylindrical tube or the like. The container may be closed at one end, e.g., a test tube for batch-wise processing, or open at both ends, e.g., a capillary or larger diameter tube for continuous processing. The container has a wall 125 and an opening for receiving the test medium being separated. The separator also comprises magnetic means represented by six magnets 127 which are equally spaced around the container. Suitable means may be provided for supporting the container 123 within the central portion of the separator.

FIG. 4 illustrates a variation of the magnetic separator of the invention illustrated in FIGS. 1A–1C. In FIG. 4, the separator 221 comprises a plurality of containers 223 held by a carrier 241 and a magnetic means external to the carrier. Each container has a peripheral wall 225 and an open top. The magnetic means comprises four magnets 227 having curved faces disposed concentrically around the carrier.

The carrier 241 comprises a non-magnetic base 243, with separate non-magnetic compartments 253 fitted into the base. Each such compartment is dimensioned to support securely one of the containers 223 in an upright position such as by standing upon the base 243 or having the flared tops of the containers 223 rest upon the upper rim of the compartments.

FIGS. 5 and 6 illustrate another embodiment of the magnetic separator of the invention. The magnetic separator 321 comprises a cylindrical container 323 with openings at either end to permit the test medium being separated to flow through the container. The separator also comprises four magnets 327 which are spaced around the container with substantially equal intervals therebetween.

The container illustrated in FIGS. 5 and 6 has a peripheral wall 325 that defines an inner cross-sectional space 362 inside the container. One end of the container has an inlet port 363 that is dimensioned to permit test medium to flow into the central portion 365 of the inner cross-sectional space between the wall and the central portion. The baffles are also inclined downwardly along the direction of flow toward wall 325. Hence, in passing through the container, the magnetically responsive colloidal particles are attracted by the magnets 327 onto the baffles and toward the wall. The baffles guide the particles along to a point at which the field gradient becomes sufficiently strong to cause the particles to adhere to the wall. The container also has at least two outlets. One outlet 369 is along the periphery of the wall for collection of the particles. A second outlet 371 is aligned with the axis of the container for discharge of the residual non-magnetic test medium.

The magnetic particles may be separated from the test medium using the magnetic separator apparatus described above, after the test medium has been subjected to the magnetic field for a sufficient time to cause the magnetic particles to migrate and adhere to the container wall. The non-magnetic components of the test media may be removed by decantation or aspiration, with the container still in the separator. A buffer, a wash liquid, or the like may then be added, while the container remains within the separator, to contact the wall for washing the adhering magnetic particles substantially free of any residual non-magnetic components. If desired, the wash liquid may be removed and the process repeated. If it is advantageous to resuspend the magnetic particles, the container may be removed from the magnetic field and manipulated to allow the magnetic particles to be dislodged from the walls and resuspended in a suitable liquid medium, e.g., to facilitate analysis. The magnetic separation apparatus and methods of the invention permit advantageous use of diffusion controlled solution kinetics of the primary incubation mixture. Moreover, various analytical procedures, including quantitative determinations, may be performed on the magnetically immobilized colloid. Such steps include washes for removal of non-specifically bound substances, secondary immunochemical reactions or detection reactions (e.g., enzymatic, fluorescent or chemiluminescent reactions).

The ability to retain the magnetic particles adhered to the wall of the container after the test medium has been removed is of considerable utility. Certain operations are more efficiently carried out in this way, such as washing or rinsing the target substance, e.g., cells or labeled components of a reaction mixture, while avoiding a separate resuspension step. In addition, secondary reactions such as those involving the interaction of labeled immunoreactive agents with a target substance carried by the magnetic particles may be performed more efficiently with the particles adhered to the wall. Here again, resuspension of the colloidal magnetic particles is avoidable. Furthermore, in performing enzyme-labelled immunoassays in accordance with the present invention, substrate incubation is preferably carried out directly on the colloidal magnetic particles immobilized in the separation apparatus.

An enzyme-labeled immunoassay may be performed to determine the presence or quantity of a ligand, such as a cell-surface antigen, suspended within a test medium contained in a non-magnetic container. A quantity of colloidal magnetic particles having a biospecific receptor, such as a particular antibody for binding with the antigen, is added to the test medium along with a quantity of enzyme-linked receptor that is also specific to the ligand. The test medium is then incubated under conditions causing binding of the antigen to both the enzyme-linked antibodies and the magnetic particles. The container is then placed into a magnetic separator so that the magnetic particles are attracted toward and adhered to the interior wall of the container. The test medium may then be removed from the container while leaving behind the magnetic particles which remain adhered to the wall. The remaining material adhered to the wall may then be washed in order to remove any unbound substances. Such washing away of unbound material may be facilitated by initially controlling the concentration of magnetic particles so that material is deposited on the interior wall of the container in a substantially single layer thus avoiding entrapment of unwanted material in voids or pockets that would otherwise be formed between layers of magnetic particles. Finally, the presence or quantity of the cell-surface antigen or other ligand of interest present in the original test medium may be measured by determining the activity of the enzyme which is bound via the biospecific antibody to the antigen which in turn is likewise bound to the magnetic particles. The enzyme activity determination is preferably carried out while the magnetic particles remain adhered to the container wall, but may be performed after resuspension if desired. The determination may include standard enzyme activity measurements such as reaction with a chromogenic substance which may then be compared to a color standard or by conducting secondary immunochemical reactions or detection reactions involving the ligand.

Performing the magnetic separation method of the invention batchwise, i.e. in a steady-state system, as described above, instead of in a flow through system, has certain advantages. Immobilized magnetic particles bearing the target substances are not dislodged due to collisions with other particles. Moreover, batchwise operation eliminates dislodgment of immobilized magnetic particles due to shear forces produced by a flowing test medium. In other words, the adherence of the magnetic particles to the wall is sufficiently strong to permit washing, secondary reactions, and interactions with other reagents to occur without appreciable dislodgment of the magnetic particles from the wall. In addition, the adherence of the magnetic particles to the container wall is maintained to some extent even if the container is removed from the magnetic field before further reaction with, or treatment of the particles.

In other applications it is desirable to be able to employ a magnetic separator adapted for use in a flow through process. For example, flow through processes are very desirable for separating large quantities of material of a uniform type. Surprisingly, the separator of the invention avoids the problem of dislodged particles noted above that commonly occurs when employing a flow through process.

In general, the magnetic particles are relatively easily separated from the container wall after removal from the magnetic field. The particles may be dislodged by contacting the wall with a modified buffer solution, or a bath sonicator. Alternatively, the particles may be collected as they are dislodged from the wall with a probe sonicator.

Figure 2:
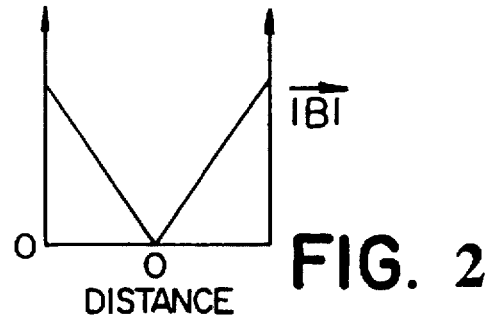
FIG. 2 is a graph of relative magnetic flux density along the line 1B versus distance.

Multipole magnetic separation devices such as those described above in which near neighbor pole faces are of opposite polarity create high gradient fields wherein the magnitude of the gradient is limited only by the field density at the pole face and the distance separating opposing poles. Compared with gradient fields produced by inducing magnetic fields on ferromagnetic material (fine wires, rods, spheres etc.) placed in external fields, the multipole devices of the invention have substantial advantage because the field strengths at the center of the opposing poles is zero (see FIG. 2). Hence, the gradients produced are only limited by the ability to produce fields greater than zero.

Figure 7A:
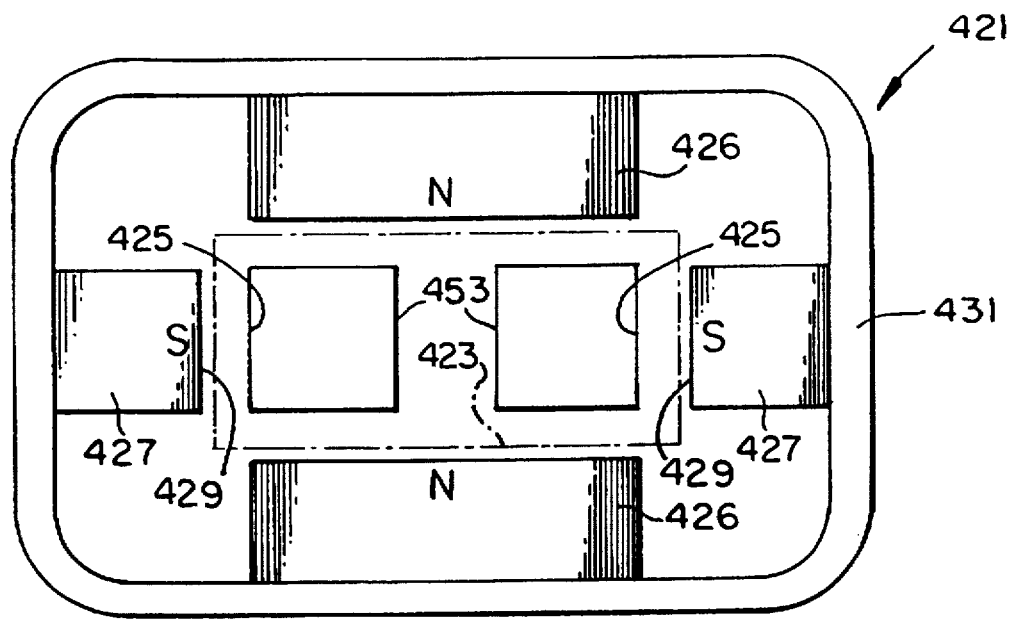
FIGS. 7A and 7B are schematic diagrams of multipolar magnetic separators having magnets of different cross-sectional area.

The performance and utility of multipole separators may be enhanced by the use of magnets of differing cross-sectional areas. Referring to FIG. 7A there is shown a schematic arrangement of a multipole separator 421 in which one pair of magnets 426 are disposed longitudinally in a horizontal plane and a second pair of magnets 427 are disposed laterally, each pair of magnets being on opposite sides of a common gap or receptacle 423, which in the present instance accommodates two containers 453. Suitable means are provided for removably supporting the containers 453 within the receptacle 423. The magnets 426 and 427 are mounted within a rectangular yoke 431. The laterally disposed magnets 427 have a smaller cross-sectional area than the longitudinally disposed magnets 426. The containers 453 are supported within the receptacle such that each of the containers is adjacent to one of the magnetic poles of smaller cross-sectional area. The larger magnets 426 are oriented such that like poles, shown in FIG. 7A as north poles, are in confrontation across the gap or receptacle 423. The smaller magnets 427 are also oriented with like poles, shown in FIG. 7A as south poles, are in confrontation across the gap or receptacle 423. The polarity of magnets 426 and 427 may be reversed without departing from the scope of the invention as long as the relative arrangement of like and unlike poles is preserved. Lines of magnetic flux within such an arrangement are more greatly concentrated at the faces of the smaller magnets than would be the case in a multipole separator having identically-sized magnets of equal strength. Hence collection of magnetically-responsive particles occurs predominately upon the interior surfaces 425 of the containers 453 that are adjacent to the smaller pole faces 429 of the magnets 427.

Figure 7B:
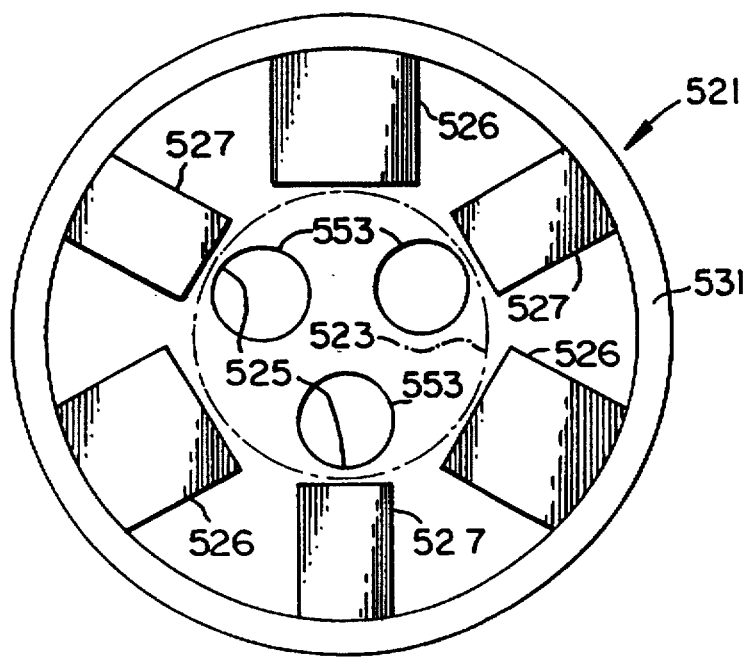

Such use of magnets of differing cross-sectional area may also be extended to other separation geometries, such as the hexapole separator 521 shown in FIG. 7B. Within hexapole separator 521, three magnets 526 and three magnets 527 are mounted upon a circular yoke 531 at alternating positions and with alternating polarities about a hexagonal gap or receptacle 523. The magnets 526 all have like poles facing the hexagonal gap, while the magnets 527 all have like poles facing the gap of a polarity opposite to the poles of the magnets 526 facing the gap. The cross-sectional area of the magnets 527 is smaller than that of the magnets 526 in order to provide a higher flux density in the gap 523 adjacent to the pole faces of magnets 527 than the flux density in the gap 523 adjacent to the pole faces of magnets 526. Such a disparity in flux density provides for preferential collection upon the interior surfaces 525 of the three containers 553 within the gap 523 that are located adjacent to the pole faces of the smaller magnets 527. The containers 553 may stand freely within the receptacle 523 or may be supported therein by an appropriately configured carrier as described in connection with FIG. 4.

Figure 8:
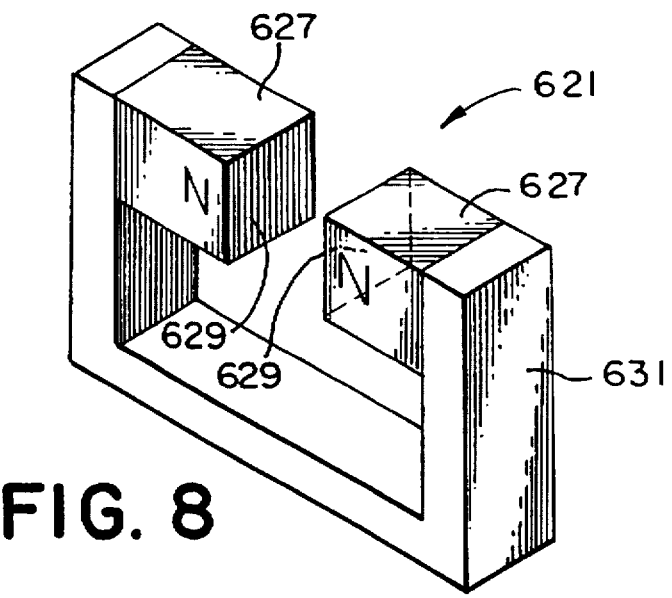
FIG. 8 is a perspective view of a magnetic separation apparatus utilizing an opposing magnetic dipole.

Several further embodiments have been found to be useful for such applications as automation of separation methods in which it may be preferable to provide a gap or receptacle in which collection containers may be displaced horizontally as well as vertically. Referring to FIG. 8, an opposing dipole separator 621 includes two magnets 627 having like pole faces 629 in confrontation across a gap or receptacle which allows lateral as well as vertical insertion of a separation vessel (not shown) which is supported between the two magnets 627. The separator shown in FIG. 8 also allows insertion and removal of the vessel at a range of angles having directional components defined by the lateral and vertical axes. Such an opposing dipole arrangement may be constructed by, for example, mounting permanent magnets upon a yoke 631. The magnetic field strength between the pole faces varies from zero along a plane defined by points equidistant from the pole faces of the magnets to a maximum value upon the pole faces. The transverse magnetic field gradient provided thereby causes collection of magnetically-responsive particles upon the interior surfaces of the vessel which are adjacent to the pole faces 629. The pole faces 629 may be flat as shown or contoured to conform to variously shaped vessels, such as by tapering. Conforming the shape of the pole faces to the shape of the vessel provides a uniform magnetic field distribution across the collecting surfaces of the vessel and thus enhances uniformity of the particles deposited on the collection surface.

Figure 9:
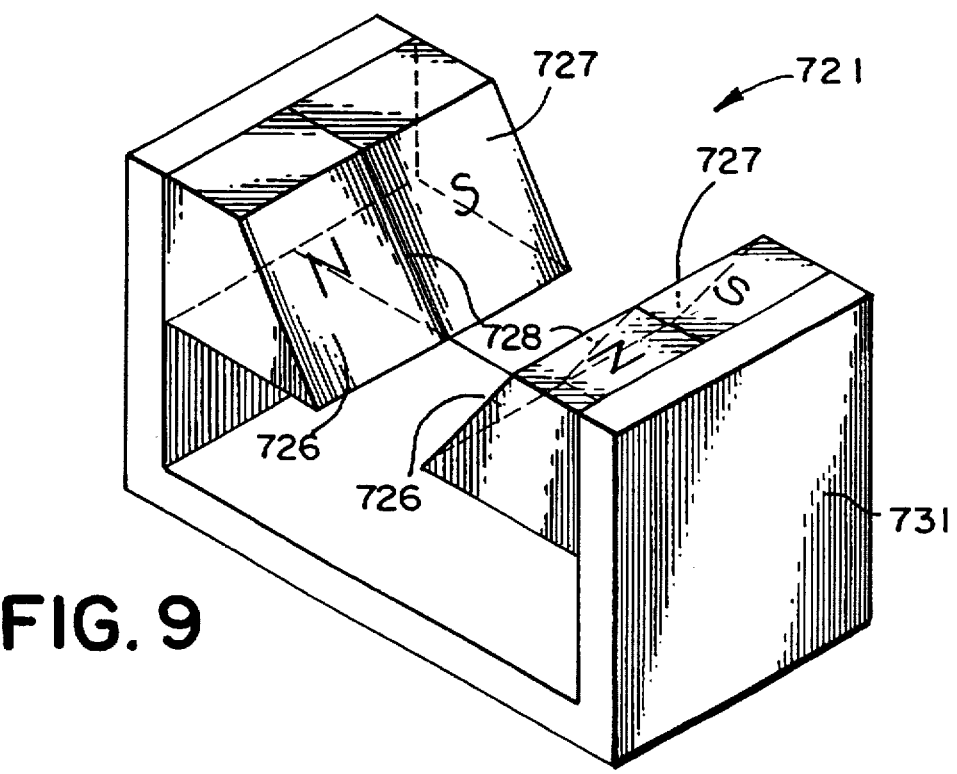
FIG. 9 is a perspective view of a magnetic separation apparatus utilizing a multiple opposing dipole.

A magnetic arrangement shown in FIG. 9 such as a double dipole separator 721 provides greater localization and intensification of the magnetic gradient. A pair of opposing dipoles 727 and 726 of complementary polarity are mounted upon a yoke 731 such that junctions 728 are located between neighboring pole faces on each side of the gap or receptacle. Such an arrangement provides confinement of the magnetic field to the regions within the receptacle about the junctions 728 to a greater extent than the magnetic field generated within the single opposing dipole separator discussed in connection with FIG. 8. The complementary pairs of dipoles may be arranged in an opposing orientation wherein the north pole of one pair confronts the north pole of the other pair as shown or in an attracting orientation wherein the north pole of one pair confronts the south pole of the other pair. A non-magnetic container (not shown) may be supported between the sloping surfaces of the magnets 726 and 727 or may be supported by other means such as by resting upon the yoke 731.

Figure 10:
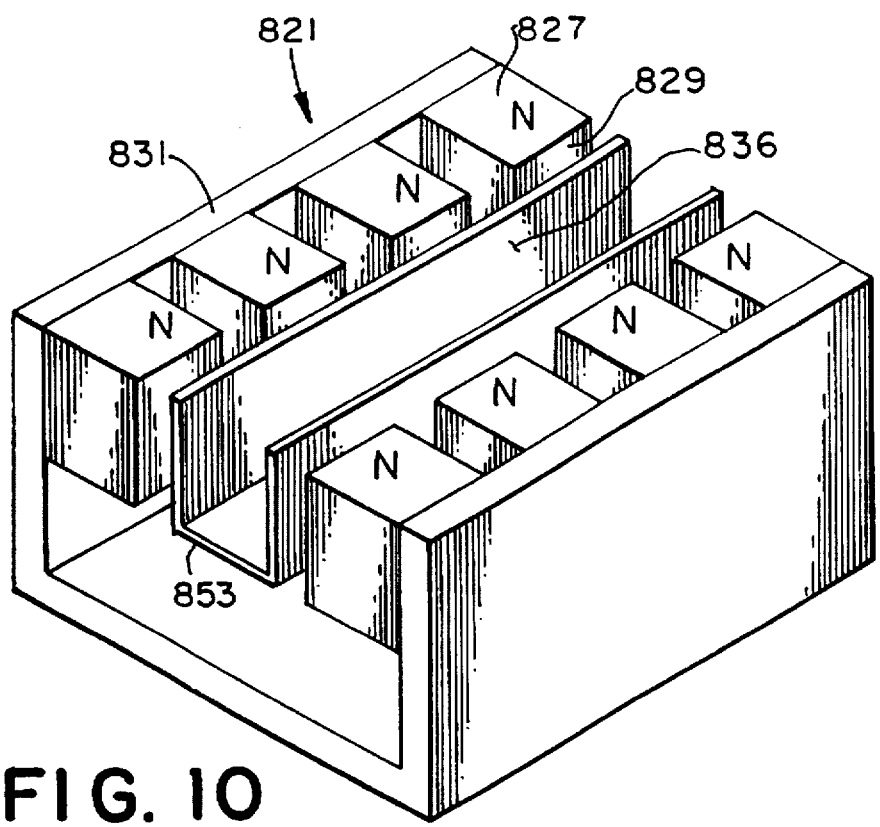
FIG. 10 is a perspective view of a magnetic separation apparatus utilizing a series of opposing dipoles.

Opposing dipoles as discussed in connection with FIG. 8 or complementary pairs of opposing dipoles as discussed in connection with FIG. 9 may be multiply disposed along a central trough such as central trough 853 shown in FIG. 10. A yoke 831 extends longitudinally to provide a suitable mounting for a longitudinal array of confronting magnetic poles 829. The elongated separator 821, shown having magnets 827 forming several opposing dipoles along the length of the trough 853 provides enhanced separation efficiency for applications such as continuous flow separations. An inlet and outlet (not shown) are provided to allow a test medium containing magnetically-responsive particles to flow along the central trough 853. Suitable means are provided to support the central trough 853 and to permit insertion and removal of the central trough into the gap between the magnets 827. As the test medium flows through the trough 853, magnetically-responsive particles are separated from suspension and are caused to adhere to those portions of the interior surface of the central trough, such as location 836, that are adjacent to a pole face, such as pole face 829, or adjacent to a junction between complementary pole faces of a dipole pair such as junction 728 discussed in connection with FIG. 9. The orientation of the magnets 827 may be opposing, attracting, or may alternate polarity periodically or aperiodically.

Figure 11:
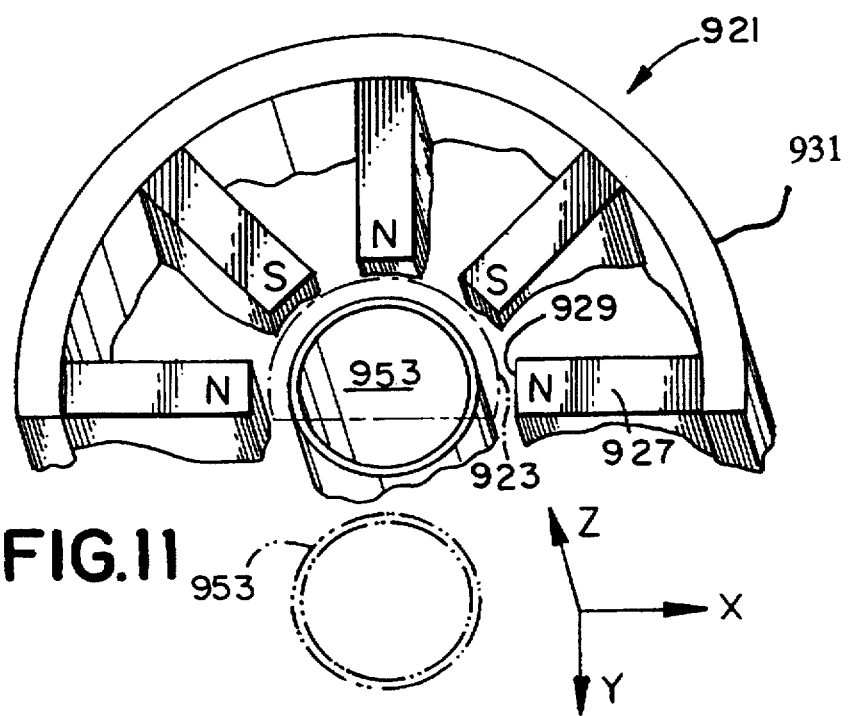
FIG. 11 is a schematic diagram of a magnetic separation apparatus utilizing an asymmetric multipole.

Ease of lateral, or angular, access to the receptacle may be incorporated into a multipolar separator geometry as shown in FIG. 11 which schematically illustrates the magnetic configuration of an asymmetric multipole separator 921. The asymmetric multipole separator 921 has several magnets 927 mounted on a yoke 931 so as to define a gap or receptacle 923 about which the magnetic pole faces are radially positioned. The gap or receptacle 923 is not completely surrounded by the arrangement of magnets 927 and hence a container, such as container 953, may be inserted into the gap and removed from the gap along the Y-axis as well as the Z-axis and at a range of angles having directional components defined by the Z-axis and the Y-axis. The magnets 927 may have identical polarity, may include complementary opposing pairs of magnets, or may be of alternating polarity as shown. The lateral accessibility of an asymmetric separator may also be provided in other multipolar arrangements having a greater or lesser number of magnets than shown in which the supporting yoke for the magnets only partially surrounds the receptacle. Magnetic poles of differing cross-sectional areas as described in connection with FIGS. 7A and 7B may also be employed in asymmetric multipolar separators to provide intensification of magnetic field gradients as may be preferred in particular applications.

When a droplet of suspended magnetic particles is introduced into a magnetically inert fluid (i.e., a fluid that is either non-magnetic or weakly magnetic compared to the ferrophase), the magnetic particles within the droplet are subject to influences tending to disperse the particles and are also subject to influences tending to aggregate the particles. An important dispersive influence is thermal diffusion. If the particles have a sufficient magnetic moment, the dispersive influence of diffusion can be balanced by mutual magnetic attraction between particles and, to a lesser extent, by cohesive forces within the liquid component of the ferrofluid. Such balanced interaction between the particles can cause the droplet to form a lattice-like structure, or ferrophase, that remains distinct from the inert fluid. In addition to inhibiting diffusion of the magnetic particles into the inert fluid, the non-magnetic components of the suspension can be inhibited from diffusing out of the ferrophase by interaction between the magnetic particles and such non-magnetic components. Such interaction may be due to viscous effects or to polar electrostatic effects, such as solvation and charge interactions. Hence, a two-phase system, comprising an inert fluid and a ferrophase, can be formed and maintained.

Upon the application of a magnetic field, it is believed that magnetic interaction between the magnetic particles increases. The increased magnetic attraction causes increased stress within the ferrophase, since some particles will experience stronger attraction and other particles will experience stronger repulsion depending upon the positions of the particles within the lattice-like structure. Whether such internal stress is sufficient to destroy the integrity of the ferrophase depends upon the strength of the applied field and the relative importance of fluid viscosity and/or polar electrostatic effects upon the stability of the ferrophase. Under a relatively weak magnetic field gradient, the ferrophase will move relative to the surrounding inert fluid in the direction of increasing magnetic field strength. The non-magnetic components of the ferrofluid will be retained within the ferrophase, and will be transported by the movement of the ferrophase. If the magnetic field intensity continues to increase as the ferrophase moves in the direction of the gradient, the internal stress in the ferrophase will eventually destroy the integrity of the ferrophase and release the non-magnetic component of the ferrophase in the high magnetic field intensity region of the apparatus.

Figures 12A, 12B:
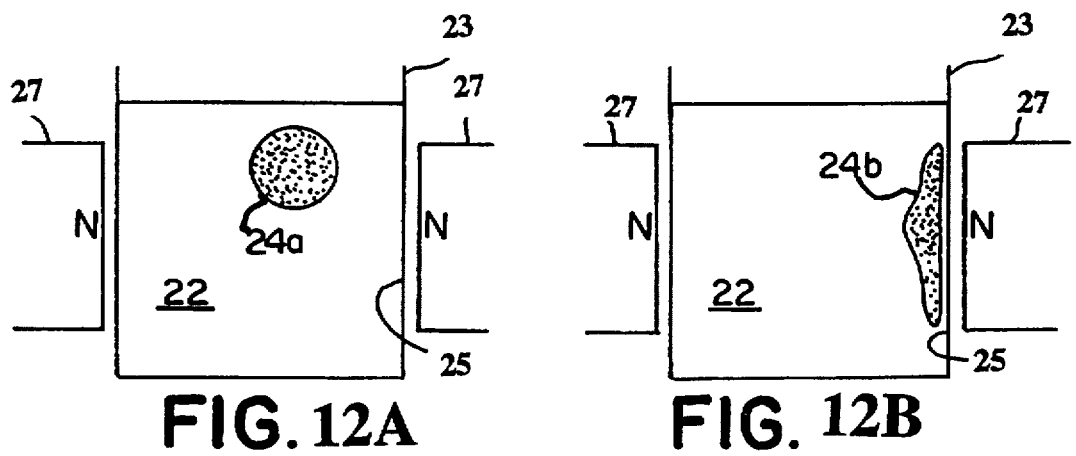
FIGS. 12A–12C are elevational sectional diagrams of the apparatus of FIG. 1A representing successive stages of a multi-phase separation process.

In FIG. 12A, there is shown a non-magnetic container 23 that is positioned between magnets 27 of an HGMS apparatus. Within the container 23 is an inert fluid 22. The composition of the fluid 22 is preferably a buffer solution that is selected to be physiologically compatible with the test medium, or a component thereof, from which a target substance is to be separated. A droplet of magnetic particle suspension, selected to have phase-forming properties, is introduced into the inert fluid 22 and forms ferrophase 24a therein. Such a droplet may be introduced, for example, by pipetting a sample of magnetic particle suspension into the container 23.

The magnetic particles in the ferrophase 24a may have a receptor thereon for binding specifically with a target substance in the carrier fluid (i.e. the liquid component of the ferrophase). Alternatively, the magnetic particles may have a common capture agent thereon for binding with one or more receptors of a common class of receptor (e.g., immunoglobulin) that are specifically bound to one or more target substances in the carrier fluid. Generally, the ferrophase 24a comprises a non-magnetic component and a magnetically-responsive component, which includes magnetic particles, and wherein the target substance is bound to the magnetic particles.

With continued reference to FIG. 12A, the relatively weak magnetic field in the vicinity of the ferrophase 24a contributes to the stability of the ferrophase 24a. The field gradient causes the ferrophase 24a to move toward the peripheral wall 25 of the container 23. In addition to being selected on the basis of phase-formation, the magnetic.particles are selected to have sufficient viscous and/or polar electrostatic effect to retain the non-magnetic component thereof within the ferrophase 24a as the ferrophase 24a moves toward the wall 25. The movement of the ferrophase 24a is very rapid relative to the movement of individual magnetic particles in a single-phase system as has been discussed in connection with FIG. 1B. One reason for such relatively rapid movement is that the viscous effect between the ferrophase and the inert fluid in the two-phase system is considerably less pronounced than the total viscous effect between all of the magnetic particles and the test medium in the single-phase system.

Figure 12C:
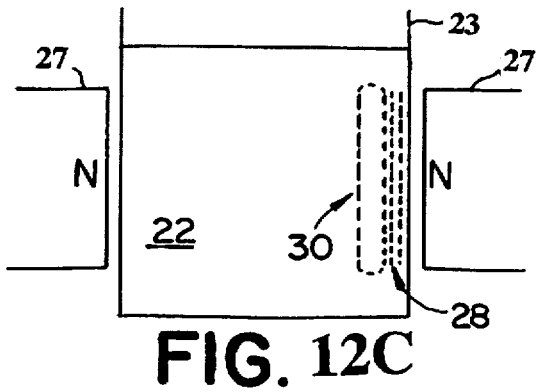

Preferably, the container 23 and the surrounding magnets are arranged such that the magnetic flux density along at least a broad portion of the wall 25 is relatively uniform, while the flux density increases in a direction toward, and the gradient thereof substantially perpendicular to, the wall 25. Hence, as shown in FIG. 12B, the ferrophase will deform to approximate the shape of the uniform field region along the wall 25 as the ferrophase approaches the wall, as indicated by the shape of the deformed ferrophase 24b. As the ferrophase 24b becomes thin and moves close to the wall 25, the high magnetic field intensity in the vicinity of the wall overcomes the stabilizing influences within the ferrophase 24b, hence the magnetic particles are pulled out of the ferrophase 24b. The resulting disintegration of the ferrophase 24b is shown in FIG. 12C wherein the magnetic particles are thinly and uniformly deposited in a layer 28 upon a broad portion of the wall 25. The non-magnetic component of the magnetic particle suspension, at least initially, is released into the magnetically inert phase and will be concentrated in a region of the inert fluid 22 generally designated as enriched region 30.

Since the magnetic particles are preferably collected in a broad thin layer 28 on the wall 25 of the container 23, the quantity of particles within the ferrophase can be controlled to result in a sparse distribution of collected particles upon the wall 25. Such collection over a broad portion of the wall 25 reduces the formation of thick agglomerations, clumps, or spots which would otherwise entrap non-magnetic components of the magnetic particle suspension in interstices between the collected particles. Additionally, since the magnetic particles are initially transported to the high gradient region en masse within the ferrophase prior to the disintegration of the ferrophase, the efficiency of separation between the magnetic and non-magnetic components of the magnetic particle suspension is greatly enhanced relative to single-phase methods.

Yet another advantage of the two-phase method relative to single-phase methods is a relaxation of geometrical constraints that have hitherto limited the useful size of external HGMS separators. For example, use of a multi-phase method eliminates the need to obtain a high intensity field within a relatively large volume of the separation chamber. A high intensity field, sufficient for separating the components of the magnetic particle suspension, is only required in a region immediately adjacent to the collection surface. The remainder of the magnetic field extending within the interior of the separation chamber is only required for attracting the ferrophase toward the collection surface and providing sufficient magnetization of the particles within the ferrophase to maintain the integrity of the phase during transport within the inert fluid.

In alternative embodiments, the order in which the inert fluid and the ferrophase are introduced into the separation container may be reversed from that described above. Similarly, it is not necessary for the separation container to be positioned within the separation apparatus when the ferrophase is established in the inert fluid. We have found that suitable phase-forming magnetic particles will establish a ferrophase, within a magnetically inert fluid, that is resistant to mild agitation, such as may occur when a two-phase system within a non-magnetic container is introduced into the separation apparatus.

Figure 13:
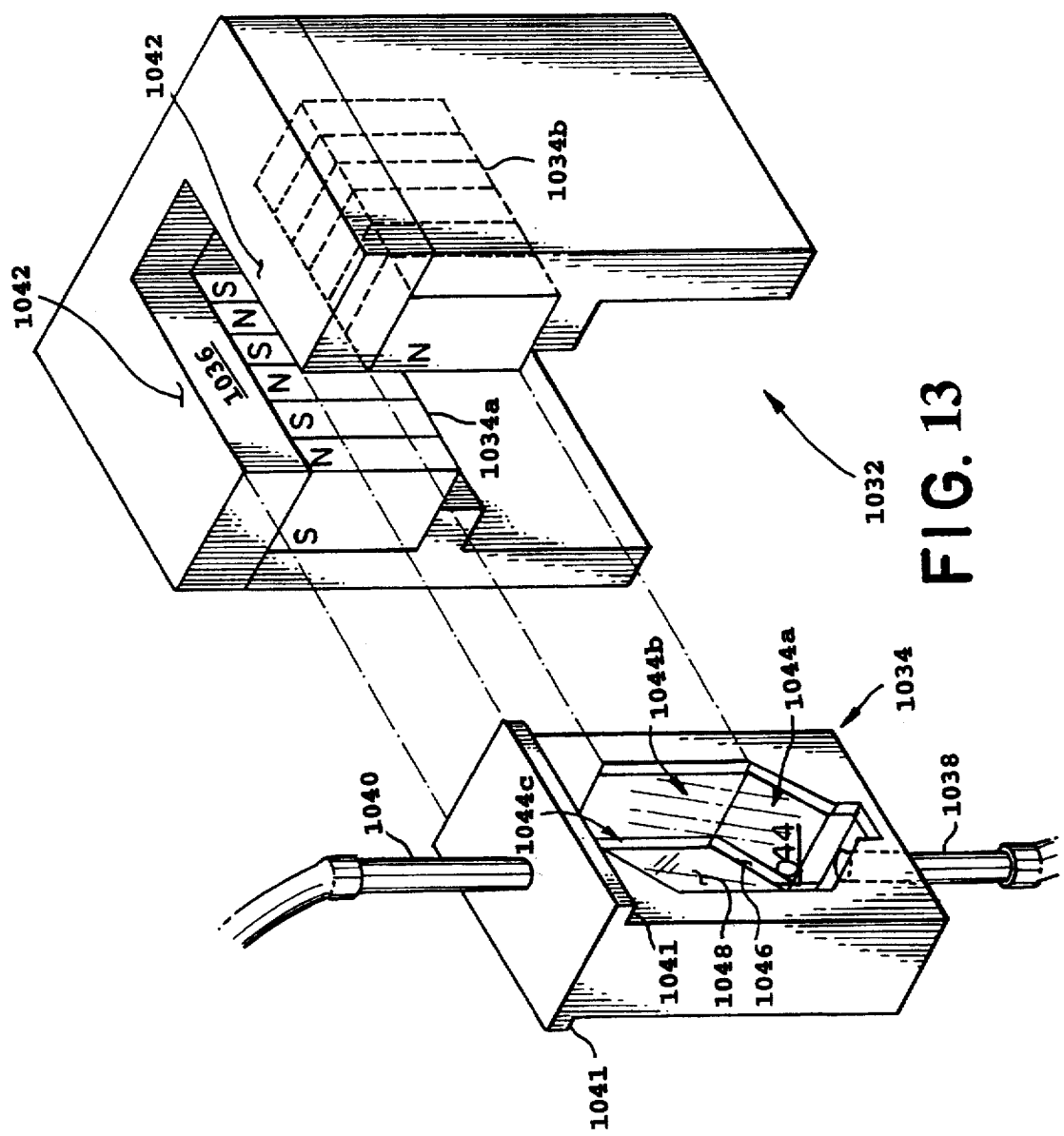
FIG. 13 is a perspective view of an apparatus for performing flow through separations in accordance with the invention.

In another alternative embodiment, it has been found that the multi-phase separation method is suitable for performing separations on a continuous, or flowthrough, basis. Referring now to FIG. 13, there is shown a flowthrough separation apparatus, generally designated separator 1032, and a non-magnetic flowthrough vessel 1034. The flowthrough vessel 1034 is adapted to be removably inserted into a vertical slot 1036 within the separator 1032.

The flowthrough vessel 1034 includes an inlet port 1038 for introducing fluid into a plenum 1044. The flowthrough vessel is also provided with an outlet port 1040 for conducting a flow of fluid out of the plenum 1044. The plenum 1044 includes a lower triangular cavity 1044a, a central rectangular cavity 1044b, and an upper triangular cavity 1044c. A pair of flanges having outwardly extending surfaces 1041 are attached to the vessel 1034, so that the surfaces 1041 rest upon upper surfaces 1042 of the separator 1032. When the vessel 1034 is inserted into the separator 1032, the vessel 1034 is supported within slot 1036 by the surfaces 1041.

The separator 1032 includes two arrays of confronting magnets 1034a and 1034b. The magnets 1034a are mounted adjacent to one another within the separator 1032 and facing one side of the slot 1036 with alternating polarity. The magnets 1034b are mounted upon the separator to face the other side of the slot 1036, thus confronting the magnets 1034a. The polarity of corresponding pairs of magnets 1034a and 1034b is the same, so that the arrays of magnets 1034a and 1034b are in a field-opposing relationship. In an alternative embodiment, the magnets may be arranged as described hereinabove in connection with FIG. 10.

During a separation procedure, the vessel 1034 is situated within the slot 1036 so that the peripheral wall 1046 of the rectangular portion 1044b of the plenum 1044 is adjacent to the array of magnets 1034b. The array of magnets 1034b generate a magnetic field 1044 that is relatively strong within the plenum along a broad portion of the peripheral wall 1046 and which is relatively weaker within the interior of the plenum 1044 more distant from the peripheral wall 1046. Similarly, a peripheral wall 1048 on the other side of the plenum 1044 from the wall 1046 is situated adjacent to the array of magnets 1034a. As in the arrangement discussed in connection with FIG. 1A, the field opposing relationship of the magnetic arrays 1034a and 1034b, and the alternating polarity of magnets within the arrays 1034a and 1034b provides high magnetic flux density gradients in the directions substantially perpendicular to the opposing peripheral walls 1046 and 1048. The magnetic field so generated is also characterized by no significant magnetic gradients in directions parallel to broad portions of the walls 1046 and 1048 in the central portion 1044a of the plenum 1044.

Figure 14:
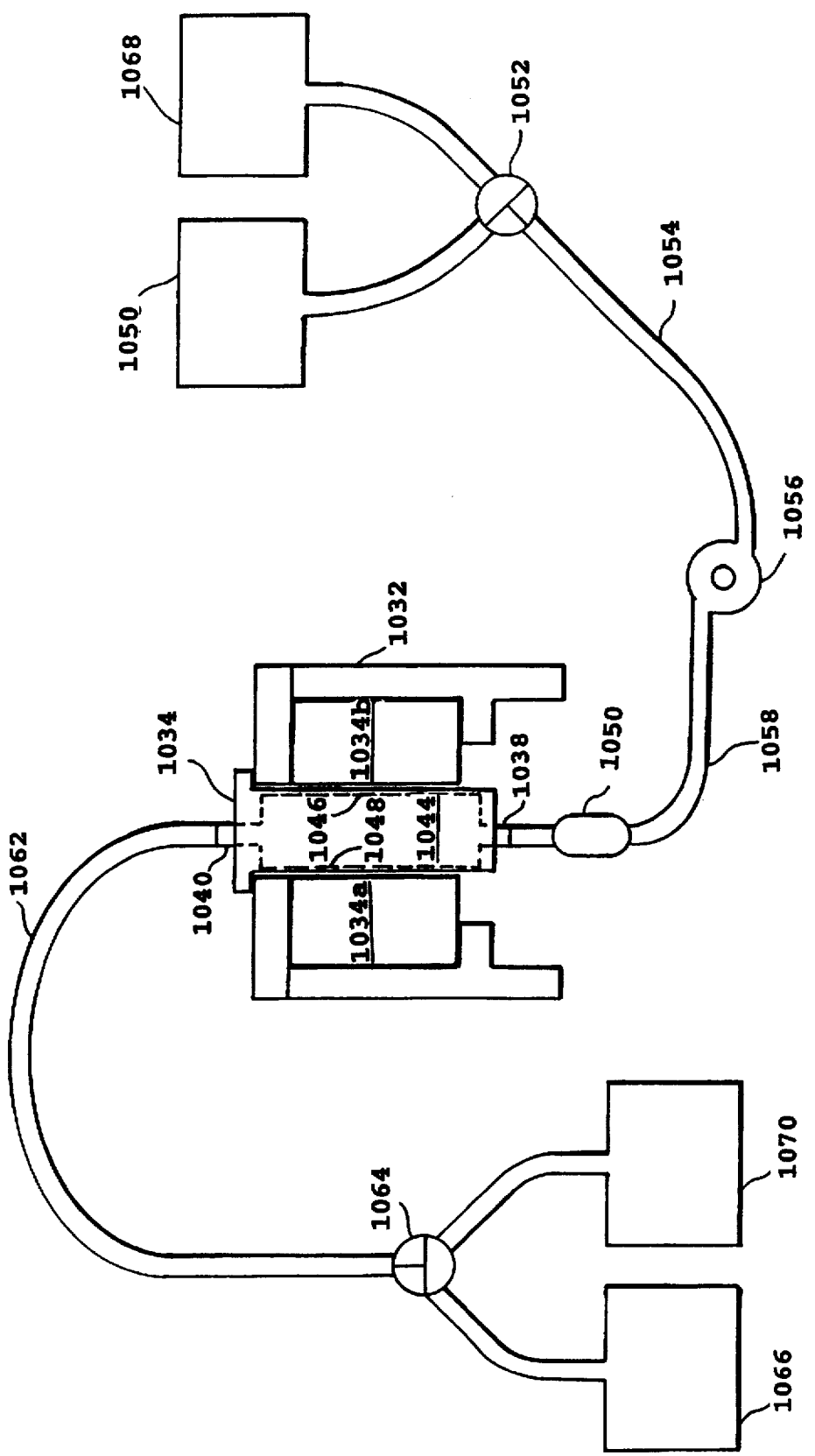
FIG. 14 is a schematic diagram of a system for performing multi-phase separations utilizing the apparatus of FIG. 13.

Referring now to FIG. 14, there is shown a preferred arrangement for performing flowthrough separations in accordance with the dual-phase principles discussed herein. The arrangement of FIG. 14 shall first be described in the context of performing a positive selection separation. In such a procedure, a source of buffer fluid, such as infusion bag 1050, is connected to a tee valve 1052. The tee valve is initially set to cause the buffer fluid from bag 1050 to flow through a conduit 1054 to a pump 1056. The pump 1056 regulates the flow of buffer fluid into a conduit 1058. The conduit 1058 is connected with the inlet port 1038 of the flowthrough vessel 1034, which is situated within the separator 1032. A bubble trap 1060 is preferably connected along conduit 1058 for removing bubbles from the fluid stream introduced into the plenum 1044 of the flowthrough vessel 1034.

In due course, the plenum 1044 is filled with the buffer fluid in order to establish the inert phase of the dual-phase system. The flow rate of the buffer fluid in this first part of the procedure, as regulated by the pump 1056, may be set to fill the plenum 1044 in a conveniently rapid manner. The flow of buffer fluid is continued so that some of the buffer fluid exits the plenum 1044 via outlet port 1040. One end of a conduit 1062 is connected to the outlet port 1040 in order to receive the flow of fluid from the outlet port 1040. The other end of conduit 1062 is connected with a tee valve 1064. The tee valve 1064 is initially set to receive fluid from the conduit 1062 and cause such fluid to be collected into a receptacle 1066.

Then, the pump 1056 is set to provide a fluid flow that is low enough to prevent strong turbulence in the conduits 1054 and 1058, and within the plenum 1044, that would disrupt the integrity of the ferrophase to be utilized in the separation procedure. The tee valve 1052 is then turned to connect the conduit 1054 with a source of a phase-forming magnetic suspension, such as an infusion bag 1068. The magnetic suspension in the infusion bag 1068 may include magnetic particles having a biofunctional coating that have been incubated with a non-magnetic fluid containing cells, cell components, or other target substances having a binding affinity for the biofunctional coating of the magnetic particles.

The magnetic suspension is then conducted along conduit 1054, through pump 1056 and conduit 1058, and into the plenum 1044 of the separation vessel 1034. Depending upon the flow rate determined by the pump 1056, the magnetic suspension may be introduced into the plenum 1044 in a continuous stream, or as a sequence of droplets. In either case, the phase forming characteristics of the magnetic suspension cause both the magnetic and non-magnetic components of the suspension to move within the plenum 1044 as a distinct phase from the inert phase that was previously established within the plenum 1044.

As the ferrophase is transported within the plenum 1044, the ferrophase is attracted as a continuous stream toward one of the peripheral walls 1046 or 1048. Individual droplets of the ferrophase may be individually attracted to either of the walls 1046 or 1048. As the ferrophase, or portions thereof, approaches the magnetic intensity region in the vicinity of a peripheral wall, the ferrophase is caused to spread out and conform to the substantially parallel contours of equal magnetic flux density along the wall. As the flattened ferrophase continues to approach the peripheral wall, it disintegrates into its constituent non-magnetic and magnetic portions. The magnetic components of the disintegrating ferrophase are rapidly collected upon the peripheral wall of the plenum 1044 in a broad, uniform pattern with no significant entrapment of the non-magnetic component. The non-magnetic component of the disintegrating ferrophase is incorporated into the inert phase of buffer solution within the plenum 1044.

After the desired quantity of the magnetic suspension from infusion bag 1068 has been introduced into the separation vessel, and the magnetic components therein have been collected upon the peripheral walls of the separation vessel, the non-magnetic component of the original magnetic suspension may be further washed out of the separation vessel as follows. The tee valve 1052 is again set to conduct a flow of buffer fluid from the infusion bag 1050 into the conduit 1054. The pump 1056 is adjusted to provide a relatively high flow rate of buffer fluid to the inlet port 1038 of the separation vessel 1034. The flow of buffer fluid is maintained for a sufficient interval to substantially wash the non-magnetic component of the magnetic suspension out of the plenum 1044 and into the receptacle 1066. During this wash step, the magnetic component of the magnetic suspension remains adhered to the peripheral walls 1046 and 1048 of the plenum 1044.

When the non-magnetic component has been substantially washed from the plenum 1044 and from the conduit 1062, the flow of buffer fluid into the plenum 1044 may be stopped while the separation vessel is removed from the separator 1032. Once the separation vessel is removed from the separator, the magnetic component of the magnetic suspension, which had been adhered to the peripheral walls of the plenum, can be resuspended within the fresh buffer. Then, the valve 1064 is set to conduct fluid from the conduit 1062 into a second collection receptacle 1070. A flow of buffer fluid is again conducted from the infusion bag 1050 and through the plenum in order to cause the resuspended magnetic component of the suspension to flow into the collection receptacle 1070 via the conduit 1062. Alternatively, a second buffer fluid, having a significantly higher viscosity and/or density than the first buffer fluid, may be used to effectively sweep the resuspended magnetic component out of the plenum and into the collection receptacle 1070. Such a second buffer fluid is preferably discrete from the original buffer fluid, so that the moving boundary between the two buffer fluids urges the resuspended particles into the conduit 1062 without significant mixing of the resuspended particles and the second buffer fluid.

In an alternative procedure, the magnetically inert phase of the two-phase separation procedure may be established by conducting an initial single-phase separation of the magnetic suspension. Such an initial separation may be formed by initially filling the plenum with the magnetic suspension at a relatively low flow rate or by filling the plenum and then stopping the flow for a sufficient period of time for single-phase separation to occur. When the single-phase separation has proceeded to the point at which the central volume of the plenum is substantially filled only with the non-magnetic component of the magnetic suspension, then the flow of the magnetic suspension to the plenum may be increased, or restarted, in order to continue the separation in a dual-phase mode. During the dual-phase mode of operation, the flow of magnetic suspension to the plenum may be substantially higher than during the initial single-phase mode since, as has been discussed, it is then no longer necessary to allow for the transport of individual magnetic components from the central portion of the plenum to the collection surface. Such a method of establishing the magnetically inert phase can be employed in both negative depletion and positive selection separations.

The arrangement shown in FIG. 14 can also be used to perform negative depletion separations, wherein it is desired to collect the non-magnetic component of a magnetic suspension. In the performance of such a method, the plenum 1044 is initially filled with a magnetically inert fluid, such as a buffer fluid, and any overflow is collected in receptacle 1066. Then, a flow of a magnetic suspension is again introduced into the plenum 1044 at a flow rate sufficient to prevent strong turbulence from damaging the ferrophase formed within the plenum 1044. When the flow of the magnetic suspension is introduced into the plenum 1044, the valve 1064 is set to collect the fluid emerging from the outlet 1040 into collection receptacle 1070. As the flow of the magnetic suspension is continuously introduced into the plenum 1044, the resulting ferrophase is attracted toward the peripheral walls. The ferrophase disintegrates and releases the non-magnetic component thereof into the buffer solution within the plenum 1044. The continued introduction of the magnetic suspension results in continuous release of the non-magnetic component of the suspension into the buffer fluid, hence the fluid stream collected in receptacle 1070 includes the non-magnetic component of the magnetic suspension and buffer fluid.

When the desired quantity of the magnetic suspension has been introduced into the plenum 1044, the valve 1052 is again set to conduct a flow of the buffer fluid from infusion bag 1050 into the plenum 1044 in order to wash any remaining non-magnetic component of the original magnetic suspension into the collection receptacle 1070. Alternatively, a second buffer fluid having a significantly greater viscosity and/or density than the first buffer fluid may be introduced into the plenum 1044 in order to sweep the non-magnetic component of the original magnetic suspension out of the plenum 1044 while avoiding further dilution of the non-magnetic component by the first buffer fluid. When the non-magnetic component of the original magnetic suspension has been washed out of the plenum 1044, through conduit 1062, and into the collection receptacle 1070, the valve 1064 is closed and the collection receptacle 1070 can be removed.

Figure 15:
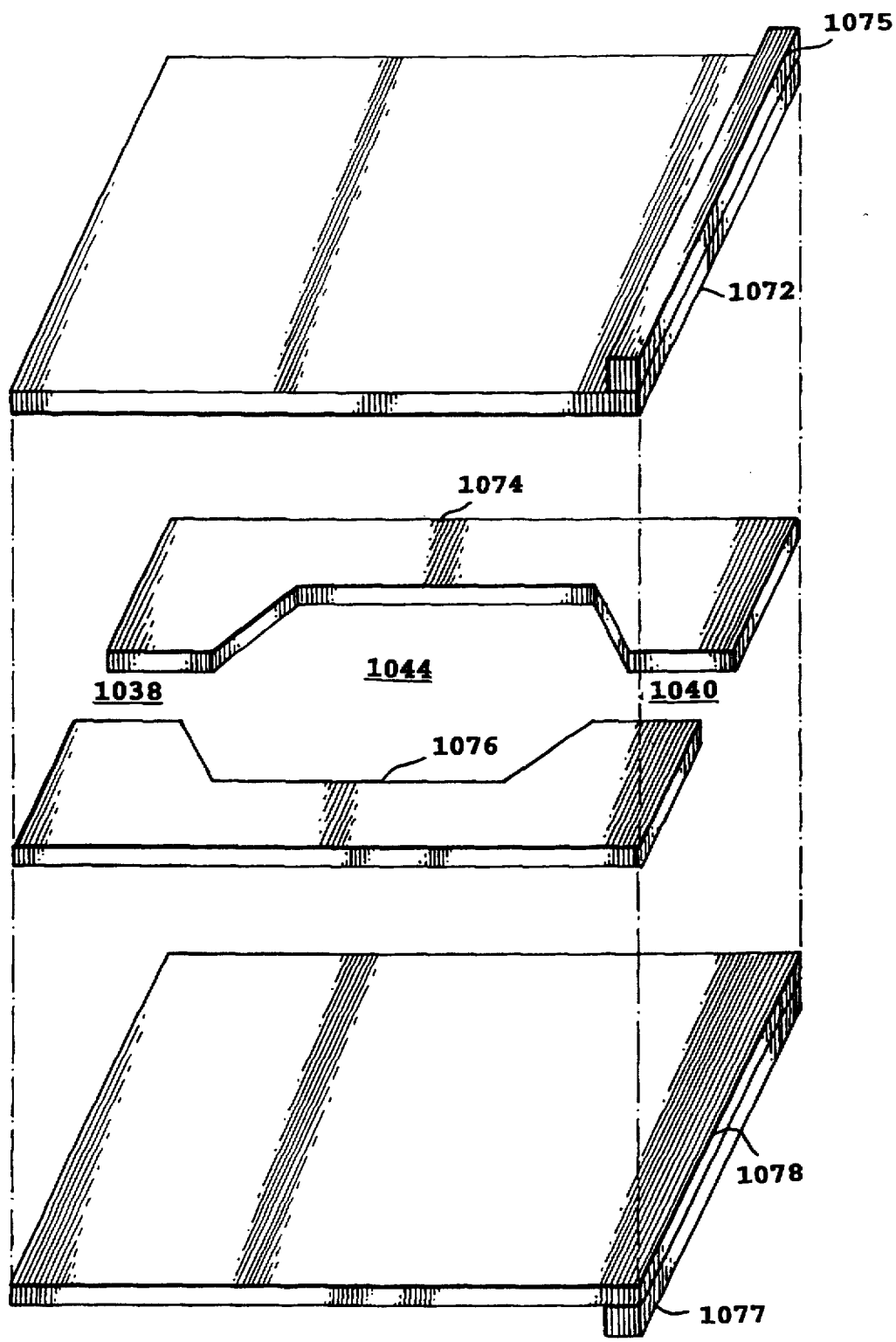
FIG. 15 is an exploded perspective view of the separation vessel utilized within the apparatus of FIG. 13.

In a preferred embodiment, the separation vessel is constructed as shown in FIG. 15. Two sheets 1072 and 1078, of a material such as "LUCITE", form the peripheral walls of the separation vessel. The sheets 1072 and 1078 are aligned with and bonded to respective upper and lower surfaces of plenum side pieces 1074 and 1076. The plenum side pieces 1074 and 1076 are shaped as shown in order to form inlet port 1038, plenum 1044, and outlet port 1040, when they are bonded to the sheets 1072 and 1078. Additionally, rectangular pieces 1075 and 1077 are bonded to the outer surfaces of the sheets 1072 and 1078 in order to form the outwardly extending surfaces for holding the separation vessel within the separator.

The advantages that may be obtained by continuous multi-phase separation relative to continuous single phase separation are similar in nature to the advantages obtained in batch multi-phase separation, i.e. greater speed, enhanced separation efficiency, and relaxation of geometric constraints upon the design of the separation apparatus. An additional advantage provided by the continuous multi-phase process is that by maintaining laminar flow in the plenum and by collecting non-magnetic component of the ferrophase via the auxiliary outlet, significantly less dilution of the non-magnetic component occurs in the flowthrough process than in the batch process. Thus, the continuous multi-phase process is particularly suitable for collection of native populations, or subpopulations, of rare non-magnetic components of the magnetic particle suspension.

It is noted that in the performance of such multi-phase separations, it is necessary to select a magnetic suspension that will have the requisite phase-forming property relative to the magnetically inert phase of the liquid system. It is additionally desirable for the magnetic suspension to possess a viscous effect and/or polar electrostatic effect sufficient to contain the non-magnetic component of the suspension within the ferrophase during transport toward the collection surface. As mentioned above, the formation of a suitable ferrophase depends upon obtaining a balance between cohesive and dispersive interactions within the magnetic suspension and relative to the magnetically inert phase of the system in which a multi-phase separation is to be performed. Several parameters which affect the influence exerted by such cohesive and dispersive interactions are: the size and mass of the magnetic particles employed, the magnetic moment of the particles, the viscosity of the non-magnetic component of the magnetic suspension, and van der Waals forces or other electrostatic interactions within the suspension. Several environmental parameters; such as temperature, turbulence, the strength of the magnetic field, and the magnetic field gradient in the separation chamber; will also affect the stability of the ferrophase and the efficiency with which components thereof may be separated.

In aqueous solutions, we have found that magnetic particles having an effective core size on the order of tens of nanometers, such as from about 50 nm to 200 nm are capable of forming stable ferrophases at room temperature and at concentrations corresponding to an Iron-equivalent from about 0.01 mg/ml and above. At the lower concentrations, turbulence becomes an important determinant of the stability of the ferrophase. At larger particle sizes, the magnetic interaction between the particles becomes strong enough that the dispersive influences, such as thermal diffusion, are not sufficient to prevent the particles from agglomerating. In solutions of greater viscosity, larger particles and/or lower concentrations of particles may be satisfactorily employed to form and maintain stable ferrophases.

Electrostatic interactions among the particles, and between the particles and the non-magnetic fluid component of the magnetic suspension can, in aqueous solutions of biological components, be reduced by adding casein, polymethacrylic acid, or other materials in order to passivate chemical coordination sites of the surface of the particles. However, the degree of influence upon ferrophase stability that may be exerted by the use of polar solvents or other fluids having a significant propensity toward van der Waals interactions, should be empirically determined in advance of performing a multi-phase separation.

The concentration of particles is most conveniently expressed in terms of iron-equivalent concentration since, in separations employing receptor-ligand binding, more than one particle may bind to a particular ligand. For example, a cell membrane may possess numerous sites to which a receptor-coated magnetic particle may attach. The term "iron-equivalent" is used herein to denote the mass of iron corresponding to the magnetic relaxivity of the actual material used to form the core of the magnetic particles. Example 1 hereinbelow demonstrates ferrophase separation conducted using unbound magnetic particles. Other examples hereinbelow demonstrate ferrophase separation conducted using bound magnetic particles bound to various target substances.

Figure 16:
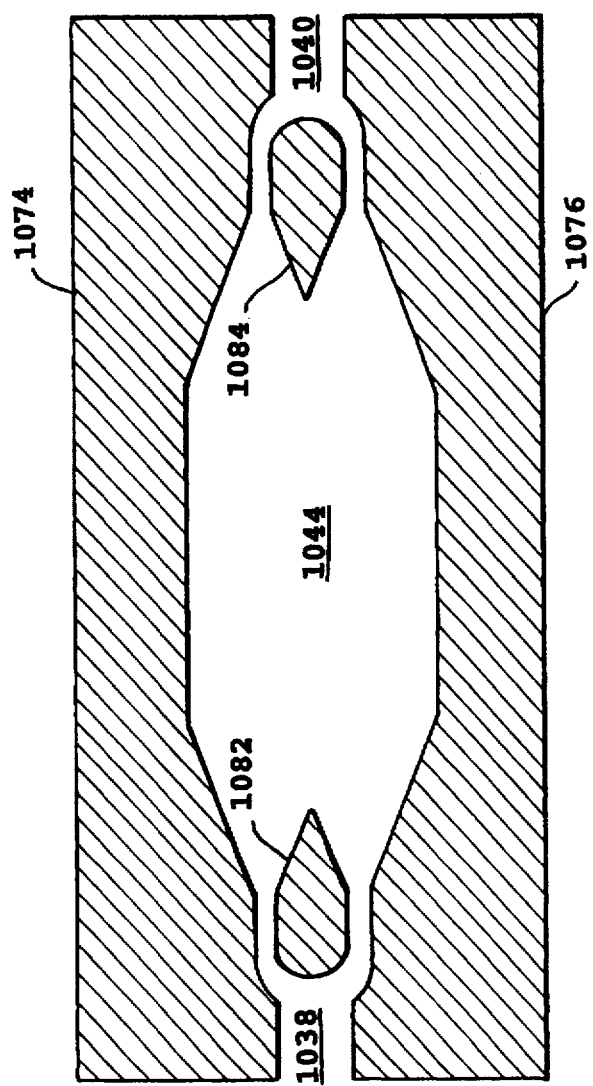
FIG. 16 is a sectional view of an alternative flow through separation vessel having reduced turbulence.

At the lower concentrations, turbulence becomes an important determinant of the stability of the ferrophase. Using the separation apparatus shown in FIG. 14, we have found that aqueous concentrations of magnetic particles on the order of less than 0.010 mg Fe/ml should be introduced at a flow rate of below 1 ml/min. At higher concentrations, such as above 0.010 mg Fe/ml, the magnetic suspension can be introduced into the plenum at up to 10 ml/min. The dimensions of the rectangular portion of the plenum are preferably 1.2 inches wide, 2.8 inches long, and 0.25 inches deep. As can be appreciated, it is desirable to supply fluid to the separation vessel via standard laboratory tubing. Thus, the cross-sectional width of the fluid flow must, at some point, be increased from the width of the tubing to the width of the broad collection surface of the plenum. Such an increase in width occurs in the triangular portion of the plenum that is adjacent to the fluid inlet port. At low magnetic particle concentrations, and/or at high flow rates, the Venturi effect in the triangular portion of the separation vessel may cause undesirable eddy currents or turbulence that could damage the integrity of the ferrophase. A preferred manner in which such turbulence may be reduced is shown in FIG. 16. In addition to the plenum side pieces 1074 and 1076, a hydrodynamic damping structure, such as a spoiler 1082, is positioned adjacent to the inlet port 1038 in order to promote laminar flow within the plenum 1044. A similar spoiler 1084 is positioned adjacent to the outlet port 1040. The separation vessel of FIG. 16, referred to hereinafter as a "dual channel" separation vessel, provides the ability to form stable ferrophases at reduced particle concentrations and/or higher flow rates relative to the separation vessel 1034 of FIG. 13. Other hydrodynamic damping structures may be effectively utilized within a flow through separation vessel to achieve similar results. For example, in an alternative embodiment, a plurality of cylindrical obstructions, or baffles, are vertically positioned at the locations occupied by spoilers 1082 and 1084 in FIG. 16.

The range of magnetic field gradients that have been successfully used to attract the ferrophase to the vicinity of the peripheral wall of the separation vessel range from about 3 KGauss/cm to about 20 KGauss/cm. These gradients were obtained by using rare earth permanent magnets, such as Nd-Fe-B magnets, providing a measured field of about 4 KGauss at the pole faces thereof. The gradient in the separation chamber can be adjusted by selecting an appropriate gap spacing between opposing magnets on either side of the chamber.

While various aspects of the present invention have been described and exemplified above in terms of certain preferred embodiments, various other embodiments may be apparent to those skilled in the art. For example, the method of the invention is suitable for scale-up to accommodate large volumes of material for various industrial processing applications, especially involving biological materials. Accordingly, the invention is not limited to the embodiments specifically described and exemplified, but is capable of variation and modification, within the scope of the appended claims.

The terms and expressions which have been employed are used as terms of description and not of limitation. There is no intention in the use of such terms and expressions of excluding any equivalents of the features shown and described or portions thereof. It is recognized, however, that various modifications are possible within the scope of the invention as claimed.

That which is claimed is:

1. A magnetic separation apparatus, comprising:

a flowthrough vessel;

mounting means for supporting said vessel and having a slot therein for receiving said vessel;

a first array of magnets mounted upon the mounting means along one side of the slot and arranged adjacent one another to face the slot with alternating polarity;

a second array of magnets mounted upon the mounting means along the opposite side of the slot from said first array, said second magnets arranged adjacent one another to face the slot with alternating polarity, each of said magnets in said second array confronting and magnetically opposing one of said magnets in said first array; and wherein said vessel comprises a plenum, an inlet port for introducing fluid into said plenum, and a hydrodynamic damping structure located between said inlet port and said plenum for reducing turbulence in said fluid.

* * * * *